(12) United States Patent
Matsumoto et al.

(10) Patent No.: US 9,943,815 B2
(45) Date of Patent: Apr. 17, 2018

(54) MIXING DEVICE INCLUDING A DISK-SHAPED MIXING SECTION INCLUDING PINS PROTRUDING FROM THE DISK-SHAPED MIXING SECTION, MIXTURE FLUID PRODUCTION DEVICE MIXTURE FLUID PRODUCTION METHOD, AND MIXTURE FLUID, OXYGEN-CONTAINING WATER AND ICE PRODUCED BY THE SAME

(75) Inventors: Takaaki Matsumoto, Kawasaki (JP); Junichi Kumakura, Kawasaki (JP)

(73) Assignee: TAKAAKI MATSUMOTO, Kanagawa (JP)

( * ) Notice: Subject to any disclaimer, the term of this patent is extended or adjusted under 35 U.S.C. 154(b) by 1189 days.

(21) Appl. No.: 13/994,469

(22) PCT Filed: Dec. 15, 2011

(86) PCT No.: PCT/JP2011/079103
§ 371 (c)(1),
(2), (4) Date: Aug. 30, 2013

(87) PCT Pub. No.: WO2012/081682
PCT Pub. Date: Jun. 21, 2012

(65) Prior Publication Data
US 2013/0337081 A1   Dec. 19, 2013

(30) Foreign Application Priority Data

Dec. 15, 2010   (JP) .................................. 2010-279153

(51) Int. Cl.
*B01F 3/04*   (2006.01)
*B01F 5/06*   (2006.01)
(Continued)

(52) U.S. Cl.
CPC .......... *B01F 11/0258* (2013.01); *A01G 25/00* (2013.01); *A01K 7/00* (2013.01);
(Continued)

(58) Field of Classification Search
CPC .............. B01F 11/0258; B01F 11/0208; B01F 5/0604; B01F 3/04503; B01F 2003/04879; B01F 2215/0431; B01F 2215/0468; A01G 25/00; B65B 1/00; A01K 7/00; A61K 33/00; C02F 1/688; F25C 1/20
USPC ....................................... 366/181.5, 336–341
See application file for complete search history.

(56) References Cited

U.S. PATENT DOCUMENTS 6,447,158 B1 *   9/2002   Farkas .................. B01F 5/0471
                                                        366/169.1
6,568,845 B1 *   5/2003   Harada .................. B01F 5/0603
                                                        366/340

(Continued)

FOREIGN PATENT DOCUMENTS

JP   53-91458   8/1978
JP   8-71393    3/1996
(Continued)

OTHER PUBLICATIONS

Machine Transaltion of JP 2004-205186A.*
International Search Report dated Mar. 27, 2012 in corresponding International Application No. PCT/JP2011/079103.

*Primary Examiner* — Charles E Cooley
(74) *Attorney, Agent, or Firm* — Wenderoth, Lind & Ponack, L.L.P.

(57) ABSTRACT

A mixing device includes a mixing section that mixes a first liquid-phase fluid with one kind or two or more kinds among a solid, a gas, and a second liquid-phase fluid different from the first liquid-phase fluid, in which the mixing section includes a supply hole for a fluid, a discharge hole for the fluid, a flow path that makes the supply hole and the discharge hole communicate with each other, and pins that protrude from the mixing section such that a fluid that includes materials to be mixed is supplied from the supply hole to the flow path, mixed by passing through the flow path with contact with the pins, and discharged from the discharge hole.

6 Claims, 16 Drawing Sheets

(51) Int. Cl.
*B01F 11/00* (2006.01)
*B01F 11/02* (2006.01)
*C02F 1/68* (2006.01)
*A01G 25/00* (2006.01)
*A01K 7/00* (2006.01)
*A61K 33/00* (2006.01)
*B65B 1/00* (2006.01)
*F25C 1/20* (2006.01)

(52) U.S. Cl.
CPC .......... *A61K 33/00* (2013.01); *B01F 3/04503* (2013.01); *B01F 5/0604* (2013.01); *B01F 11/0208* (2013.01); *B65B 1/00* (2013.01); *C02F 1/688* (2013.01); *B01F 2003/04879* (2013.01); *B01F 2215/0431* (2013.01); *B01F 2215/0468* (2013.01); *F25C 1/20* (2013.01)

(56) References Cited

U.S. PATENT DOCUMENTS

| | | | | |
|---|---|---|---|---|
| 7,258,137 B2 * | 8/2007 | Plummer | ................ | B01J 4/001 137/599.03 |
| 2006/0273476 A1 * | 12/2006 | Bagley | ................ | B01F 3/0446 261/93 |
| 2010/0147690 A1 * | 6/2010 | Audunson | ........... | B01F 3/04985 204/557 |
| 2010/0276820 A1 * | 11/2010 | Mogami | ............... | B01F 5/0604 261/74 |
| 2011/0049032 A1 * | 3/2011 | Cho | ...................... | B01F 3/0473 210/203 |
| 2011/0085945 A1 * | 4/2011 | Mochizuki | ........... | B01F 5/0604 422/225 |
| 2013/0157205 A1 * | 6/2013 | Hershkowitz | ............. | F23C 5/32 431/9 |
| 2013/0337081 A1 * | 12/2013 | Matsumoto | ......... | B01F 3/04503 424/600 |
| 2014/0241960 A1 * | 8/2014 | Mochizuki | ................ | B01F 5/12 422/633 |

FOREIGN PATENT DOCUMENTS

| | | |
|---|---|---|
| JP | 9-173807 | 7/1997 |
| JP | 9-187634 | 7/1997 |
| JP | 9-192465 | 7/1997 |
| JP | 2004-205186 | 7/2004 |
| WO | 2008/047958 A1 * | 4/2008 |
| WO | 2012/095457 A1 * | 7/2012 |

* cited by examiner

MIXING DEVICE INCLUDING A DISK-SHAPED MIXING SECTION INCLUDING PINS PROTRUDING FROM THE DISK-SHAPED MIXING SECTION, MIXTURE FLUID PRODUCTION DEVICE MIXTURE FLUID PRODUCTION METHOD, AND MIXTURE FLUID, OXYGEN-CONTAINING WATER AND ICE PRODUCED BY THE SAME

TECHNICAL FIELD

The present invention relates to a technique to mix, dissolve, or subdivide a liquid-phase, gas-phase, or solid-phase substance with respect to a fluid (including a gas phase, a liquid phase, or a powder and granular material; for example, water).

BACKGROUND ART

A mixing, emulsifying, or solubilizing technique is required in wide ranges, and in the past, various techniques have been proposed.

For example, a stirring homogenizer mixer is a technique to perform pulverization, dispersion, and emulsification by making a collision and a shear force act on a raw material by an impeller that rotates at high speed.

Further, a bead shot homogenizer is a technique to perform pulverization, dispersion, and emulsification of a raw material using pulverization from collisions of beads with the raw material by stirring and oscillating the raw material and the beads at high speed.

Then, a technique called a high-speed homogenizer is a technique to perform pulverization, dispersion, and emulsification by allowing a raw material to pass through a minute slit by pressurizing the raw material with high pressure or ultrahigh pressure, and using a collision and a shear force at that time.

However, in the prior art, there is a problem in that depending on the extents of mixing, pulverization, emulsification, and solubilization which are required, the entire device increases in size and becomes complicated and thus an introduction cost becomes expensive.

Further, there is a tendency that a material to be mixed, pulverized, emulsified, and solubilized is selected, and thus there is a tendency that versatility as a mixing device is lowered.

As other prior art, there is proposed a technique to produce emulsified fuel by mixing oil, water, an emulsifier, and a gas under pressurization (refer to JP-A-2010-31070).

However, since such a technique is aimed at the production of the emulsified fuel, it is not possible to apply the technique to mixing of a gas, a liquid, and a solid in general. Then, it is not possible to solve the above-described problems of the prior arts.

SUMMARY OF INVENTION

Technical Problem

The present invention has been proposed in view of the above-described problems of the prior arts and has an object to provide a mixture fluid production device capable of efficiently mixing a liquid-phase fluid with one kind or two or more kinds among a solid, a gas, and a different liquid-phase fluid, being compact, and having high versatility. Further, the present invention has an object to provide a fluid production method using the mixture fluid production device, and a fluid and oxygen-containing water and ice obtained by the production method,

Solution to Problem

A mixing device according to the invention is characterized by the following in order to solve the above-mentioned problems.

<1> A mixing device including:
a mixing section that mixes a liquid-phase fluid with one kind or two or more kinds among a solid, a gas, and a liquid-phase fluid different from the above-mentioned liquid-phase fluid,
wherein the mixing section includes
a supply hole for a fluid,
a discharge hole for the fluid,
a flow path that makes the supply hole and the discharge hole communicate with each other, and
a plurality of pins that protrudes from the flow path, and
a fluid that includes materials to be mixed is supplied from the supply hole to the flow path, mixed by passing through the flow path with the contact with the pins, and discharged from the discharge hole.

<2> The pin may generate cavitation of the fluid by ultra-vibrating with the contact with the fluid.

<3> The mixing section may have a disk shape and have a supply hole provided in the vicinity of the center and a discharge hole provided in the vicinity of an outer peripheral edge, or a discharge hole provided in the vicinity of the center and a supply hole provided in the vicinity of the outer peripheral edge.

<4> An annular row that is formed by the plurality of pins disposed on a concentric imaginary circle may be disposed in plural rows toward the outer peripheral edge from the center of the mixing section, and the pins may be disposed in a radial fashion toward the outer peripheral edge from the center of the mixing section.

<5> At least the pin of the other adjacent annular row in a radial direction of the mixing section may be disposed at an area surrounded by two straight lines that connect the centers of two adjacent pins among the plurality of pins in the annular row and the center of the mixing section.

<6> The mixing section may be provided in plural.

<7> The mixing device may further include a substantially plate-shaped central portion, wherein the mixing section is provided on the front surface side and the back surface side of the central portion.

<8> A mixture fluid production device according to the invention includes: the mixing device according to any one of the above <1> to <7>; and pressurizing means.

A mixture fluid production method according to the invention is characterized by the following.

<9> A production method of a mixture fluid that includes a liquid-phase fluid and one kind or two or more kinds among a solid, a gas, and a different liquid-phase fluid, by the mixture fluid production device according to the above <8>, the method including:
a supply step of supplying a fluid that includes materials to be mixed from a supply hole of a mixing section to a flow path by pressurizing the fluid that includes materials to be mixed, by pressurizing means; and
a mixing and discharge step in which the fluid is mixed by passing through the flow path with the contact with a plurality of pins of the mixing section and discharged from a discharge hole.

<10> In the mixing and discharge step, the pin may ultra-vibrate with the contact with the fluid that includes materials to be mixed and cavitation of the fluid may be generated.

<11> In the supply step, the fluid may be supplied at pressure of greater than or equal to 0.1 Mpa.

<12> The supply step and the mixing and discharge step may be repeatedly performed by supplying the fluid discharged from the discharge hole again from the supply hole of the mixing section.

<13> The materials to be mixed may be a liquid-phase fluid and a gas, the liquid-phase fluid may be water, and the gas may be oxygen.

<14> A mixture fluid according to the invention is produced by the method according to any one of the above <9> to <12>.

<15> Oxygen-containing water according to the invention is produced by the method according to above <13>.

<16> In the oxygen-containing water according to the invention, the dilute concentration of dissolved oxygen may be greater than or equal to 25 ppm.

<17> Oxygen-containing ice according to the invention is obtained by freezing the water according to the above <15> or <16>.

Advantageous Effects of Invention

The mixture fluid production device according to the invention can efficiently mix a liquid-phase fluid with one kind or two or more kinds among a solid, a gas, and a different liquid-phase fluid. A material to be mixed is injected under pressurization to a predetermined pressure or more, whereby the pin vibrates in an ultrasonic range, and thus cavitation is generated in the material which is in contact with the pin. Then, due to energy of the cavitation, the material which is in contact with the pin that vibrates in an ultrasonic range is uniformly dispersed in the other material to be mixed.

As a result, even if the mixing device has a compact size, the material is subjected to the action of the cavitation when passing through the mixing section, thereby being reliably mixed, pulverized, emulsified, and solubilized.

Here, in the prior art, water in which the oxygen content is increased, for example, by pressurization is provided. However, in such water, under pressurization, it is possible to maintain high concentration dissolved oxygen. However, if the water is left under atmospheric pressure, the amount of dissolved oxygen is reduced, whereby the water becomes the same as normal water (refer to FIG. 16).

In contrast, for example, in water with a very large amount of dissolved oxygen obtained by using the mixing device according to the invention, even if the water is left under atmospheric pressure, a state where the amount of dissolved oxygen is large can be maintained for a long period of time (for example, 35 days or more).

Here, in a case of the water with a very large amount of dissolved oxygen, it is possible to easily supplement oxygen into the body by drinking the water. For this reason, it is possible to easily supplement oxygen to a person who needs oxygen supply or a person who has poor lung function.

Further, the water with a very large amount of dissolved oxygen can also be used in nurture or culture of an animal, a plan, and a microorganism which need oxygen supply, other than a human being.

In addition, for example, if the oxygen-containing water produced by using the mixing according to the invention is frozen, ice which includes a large amount of oxygen inside can be produced. If the ice which includes a large amount of oxygen is used, since a large amount of oxygen is generated when the ice is dissolved, it is possible to preserve freshness when transporting, for example, a squid, an octopus, or a shellfish which respires cutaneously.

Further, according to the experiment by the inventor of the present invention, it was found that in ice with a large amount of oxygen included inside, compared to normal ice of the same size, which is ice-made in a household refrigerator, time to dissolve was longer by ten minutes or more. For this reason, if the ice with a large amount of oxygen included inside is used, since when transporting a fresh flower, a pot flower, or vegetables, a change in temperature is reduced and oxygen which is generated when the ice is dissolved is supplied, the freshness is preserved. Similarly, by putting the ice with a large amount of oxygen included inside in a transport container of a market, a fishing boat, or the others, it is possible to perform storage or transportation while preserving the freshness of fresh food, a flower, vegetables, or the others.

In addition, if the ice with a large amount of oxygen included therein is used, it is possible to realize a reduction in temperature in the soil in a high-temperature area and oxygen supply to the soil in a high-temperature area. Or, it becomes possible to suppress an increase in the temperature of seawater and also supply oxygen to the seawater.

DESCRIPTION OF EMBODIMENT

Figure 1:
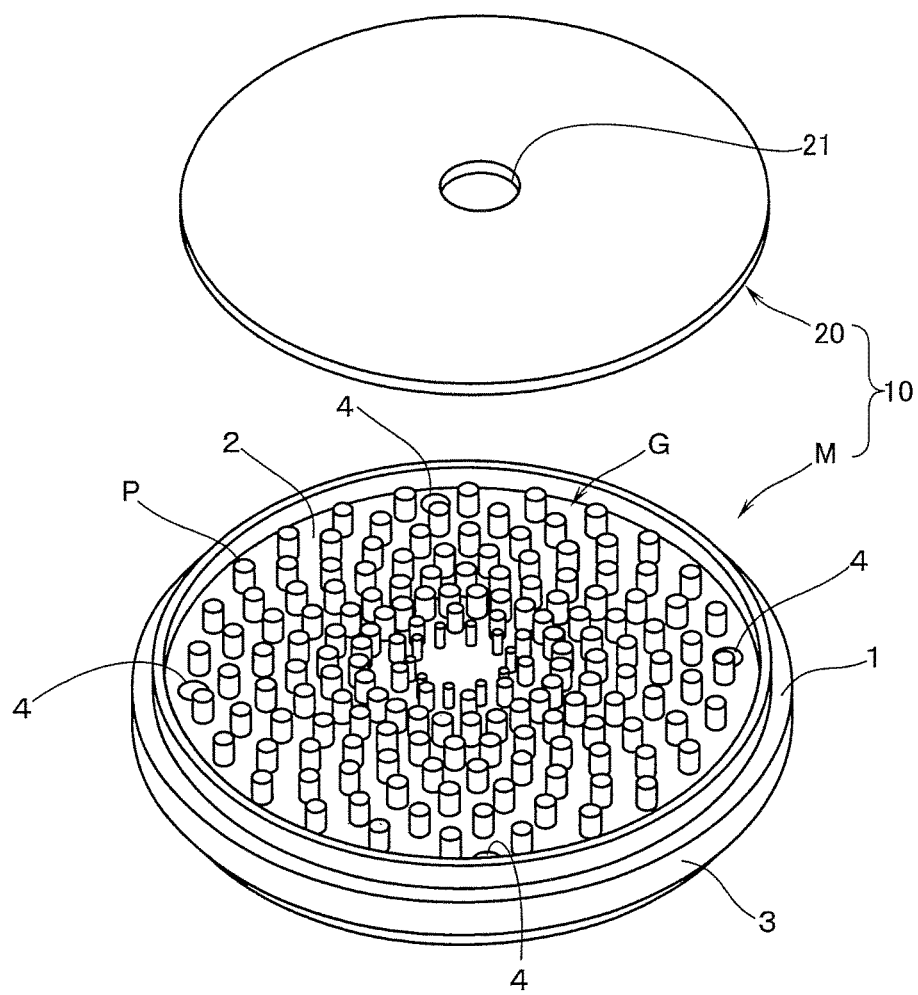
FIG. 1 is a perspective view illustrating a mixing device according to the invention.

A mixing device according to the invention is a device for mixing a liquid-phase fluid with one kind or two or more kinds among a solid, a gas, and a liquid-phase fluid different from the above-mentioned liquid-phase fluid.

As the liquid-phase fluid, for example, water, various organic solvents such as ethanol, or the like can be exemplified. As the solid, one kind or two or more kinds among a solid soluble in the liquid-phase fluid and a solid insoluble in the liquid-phase fluid can be exemplified. As the gas, for example, one kind or two or more kinds among oxygen, hydrogen, carbon dioxide, and the like can be exemplified. For example, in a case of intending to preserve the freshness of a squid, an octopus, or a shellfish, or the like, addition of sodium chloride as the solid and oxygen as the gas to water as the liquid-phase fluid, or the like is considered.

The mixing device according to the invention has a mixing section.

The mixing section has a supply hole for a fluid that includes materials to be mixed, a discharge hole for the fluid, a flow path making the supply hole and the discharge hole communicate with each other, and a plurality of pins protruding from the flow path. The fluid that includes materials to be mixed is supplied from the supply hole to the flow path, mixed by passing through the flow path with the contact with the pins, and discharged from the discharge hole as a mixture fluid.

The shape of the mixing section is not particularly limited and can be appropriately designed to a shape such as a disk shape, a columnar shape, a rectangular shape, or a spherical shape. Further, the mixing section can also be provided in plural. As a material configuring the mixing section, hard-type metal or an alloy (for example, iron or steel), a silicon-based material (glass, carbon, or the like is also included) such as diamond or ceramics, a resin material, or the like can be selected. Here, if the resin material (for example, fluorine resin) is a resin material which is applied for mixing or emulsification of organic and flexible materials, the resin material has sufficient strength.

The shape, the disposition position, and the number to be disposed of each of the supply hole and the discharge hole are also not particularly limited and can be appropriately designed in consideration of the overall shape of the mixing section, the properties of the fluid that includes materials to be mixed, a pressure condition by pressurizing means, or the like.

The flow path may have, for example, a linear shape, a curved line shape, or the like, and the shape, the length, the width, or the like thereof is not particularly limited and can be appropriately designed. Further, for example, in a case where the overall shape of the mixing section is a disk shape having a concave portion and the supply hole and the discharge hole are respectively formed in the center and an outer peripheral edge of the mixing section, the flow path can be formed as a circular space that spreads from the center to the outer peripheral edge of the mixing section.

With respect to the pin, the number to be disposed, a disposition position, the distance between adjacent pins, or the like can be appropriately designed in consideration of the disposition positions of the supply hole and the discharge hole, the shape of the flow path, the properties of the fluid that includes materials to be mixed, the content of the solid, the gas, or the like in the mixture fluid, or the like. Further, the shape of the pin can be appropriately designed to a shape such as a columnar shape or a rectangular column shape. However, from the viewpoint of the contact efficiency of the fluid with the pin, the flow of the fluid, or the like, it is preferable that the shape of the pin be a columnar shape. In addition, the height, the width (the diameter), or the like of the pin can also be appropriately designed in consideration of the shape of the flow path, the properties of the fluid that includes materials to be mixed, the content of the solid, the gas, or the like which is mixed with the liquid-phase fluid, or the like, and pins having different widths (diameters) can also be used in combination.

In addition, the pin ultra-vibrates with the contact with the fluid pressurized and supplied, thereby being able to generate cavitation of the fluid. Accordingly, the material to be mixed in the fluid is homogeneously decentralized, thereby being dissolved, dispersed, or the like in the liquid-phase fluid.

A mixture fluid production device according to the invention includes the mixing device and the pressurizing means.

It is acceptable if the pressurizing means is means capable of supplying the fluid that includes materials to be mixed at a predetermined pressure from the supply hole of the mixing section, and for example, a known pump or the like can be exemplified. For example, it is preferable that the pressurizing means can pump the fluid at pressure of, preferably, greater than or equal to 0.1 Mpa, practically, in a range of 0.1 Mpa to 10 Mpa. By push-in of the fluid from the supply hole of the mixing section, the fluid supplied and the pin come into contact with each other, whereby ultra-vibration of the pin is generated, thereby being able to generate cavitation of the fluid.

Hereinafter, an embodiment of the mixing device according to the invention will be described with reference to the accompanying drawings.

Figure 2:
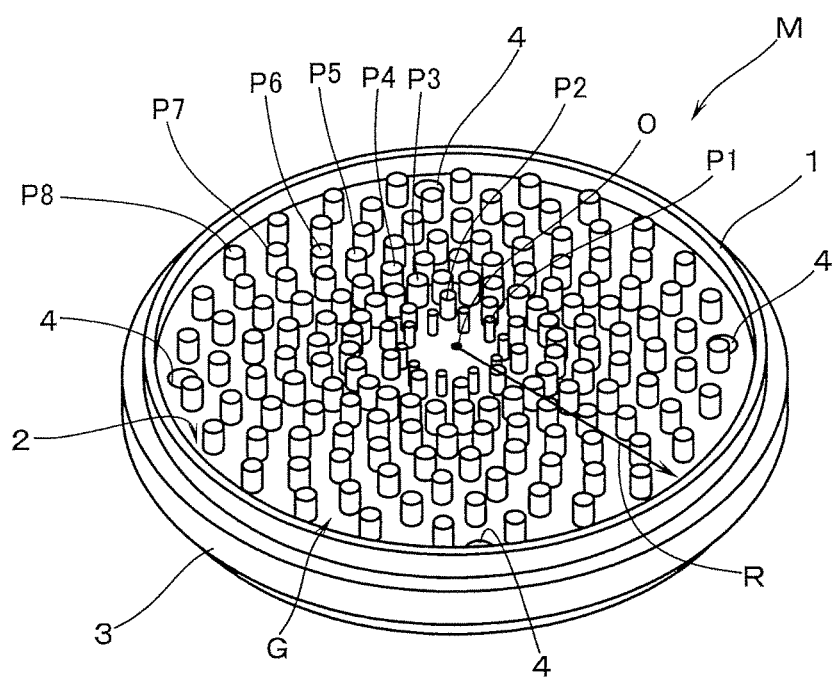
FIG. 2 is a perspective view illustrating a mixing section of the mixing device illustrated in FIG. 1.
Figure 3:
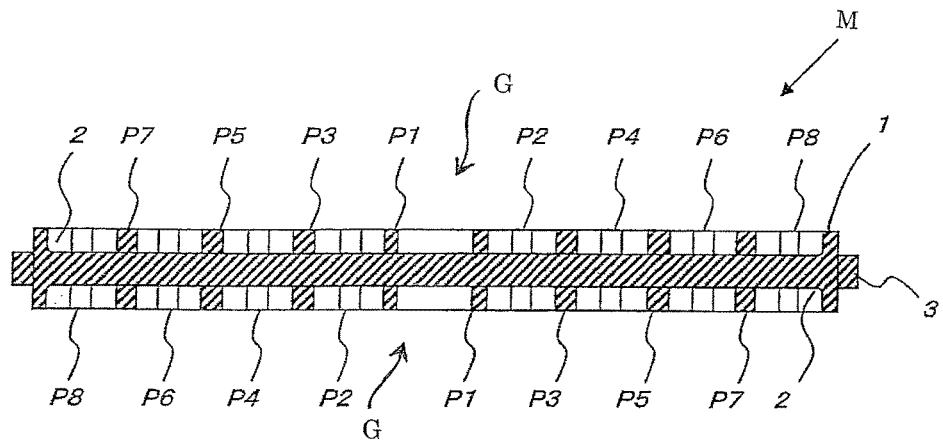
FIG. 3 is a cross-sectional view illustrating a main body (the mixing section) of the mixing device illustrated in FIGS. 1 and 2.

FIG. 1 is a perspective view illustrating the mixing device according to the invention. FIG. 2 is a perspective view illustrating the mixing section of the mixing device illustrated in FIG. 1. FIG. 3 is a cross-sectional view illustrating a main body (the mixing section) of the mixing device illustrated in FIGS. 1 and 2.

A mixing device 10 has a mixing section G having a large number of projections P, and a lid section 20 which covers the mixing section G.

The mixing device 10 has a main body M and the lid section 20.

The main body M is substantially disk-shaped and has a substantially plate-shaped central portion 3 and the mixing sections G on the front surface side and the back surface side of the central portion 3.

The mixing section G is a substantially circular area formed on the inside of the main body M and is recessed overall at an area further on the inside in a radial direction than a radially outer peripheral edge portion 1, and thus a concave portion 2 is formed. The concave portion 2 functions as a flow path for the fluid. Further, a large number of pins (projections) P protrude on the inside of the concave portion 2.

Further, although not clearly shown in FIG. 1, as shown in FIG. 3, the mixing section G of the same sort is also formed on the back surface side of the main body M. That is, a large number of pins P are provided on the inside of the concave portion 2 formed on the back surface side, and the back surface side of the mixing section G is also covered by the lid section 20 which is not shown in FIG. 1.

The substantially plate-shaped central portion 3 is provided between an area where the pins P on the front surface side of the main body M are formed and an area where a large number of pins (not shown) on the back surface side are formed (at the center in a thickness direction of a disk). That is, a large number of pins protrude from the central portion 3 on the front surface side and the back surface side of the mixing section.

As illustrated in FIG. 2, a plurality of (in a first embodiment, four) through-holes 4 is formed in a radially outer edge portion of the central portion 3. The through-hole 4 makes an area where the pins P on the front surface side (in FIG. 3, the upper side) are formed and a section where the pins P (in FIG. 3, the lower side) on the back surface side (in FIG. 3, the lower side) are formed communicate with each other.

The lid section 20 has a substantial disk shape having approximately the same outer diameter as the main body M and is formed to be capable of being fitted so as to cover each of the mixing section G on the front surface side of the main body M and the mixing section G on the back surface side.

Further, an opening 21 is formed at the center of the lid section 20, and when the concave portion 2 of the mixing section G is covered by the lid section 20, the opening 21 and a center O (FIG. 2) of the concave portion are at a corresponding position.

Then, the opening 21 of the lid section 20 and the through-hole 4 formed in the radially outer edge portion of the central portion 4 of the mixing section G function as the discharge hole or the supply hole for the fluid. Specifically, for example, the fluid that includes materials to be mixed can be supplied from the opening 21 of the lid section 20 to the mixing section G. Therefore, in this case, the opening 21 of the lid section 20 functions as the supply hole for the fluid. Then, the fluid supplied to the mixing section G passes through a flow path (the concave portion 2) communicating with the through-hole 4 of the mixing section G from the opening 21 of the lid section 20 while repeating contact with the pins P on the flow path (the concave portion 2), and is discharged from the through-hole 4 formed in the radially outer edge portion to the back surface side and also supplied to the mixing section G on the back surface side. Therefore, in this case, the through-hole 4 functions as both the discharge hole and the supply hole for the fluid. Then, the fluid supplied to the mixing section G on the back surface side passes through a flow path (the concave portion 2) while repeating contact with the pins P on the flow path (the concave portion 2) again and is discharged from the opening 21 formed at the center of the lid section 20. In this case, the opening 21 of the lid section 20 disposed on the back surface side functions as the discharge hole for the fluid.

In addition, as a method of shaping the mixing section G, for example, a method of forming a mixing section by cutting disk-shaped metal (so-called "cutting-out"), a method in which the concave portion 2 is formed by cutting disk-shaped metal, a large number (the same number as the number of pins) of female threads are provided in the concave portion 2, and a pin with a male thread cut therein is screwed on each of the female threads, a method of molding and firing a hard ceramic material (a clay-like flexible material), thereby turning it into hard ceramic, a method of cutting (performing cutting-out of) resin (for example, fluorine resin), a method of injection-molding resin (for example, fluorine resin), or the like can be exemplified.

As illustrated in FIG. 2, the center point of the concave portion 2 where a large number of pins P1 to P8 are formed is denoted by sign O.

Here, symbol P representing the pin denotes some of a large number of pins by way of example, and illustration of signs of other pins is omitted.

Here, the concave portion 2 is formed such that a planar shape is a circular shape. However, the concave portion 2 may be formed in a regular polygon or the like.

A distance from the center of the concave portion 2 to the inner wall surface of the outer peripheral edge portion 1, that is, the radius of a circle of a planar shape of the concave portion 2 is denoted by sign R in FIG. 2.

Figure 4:
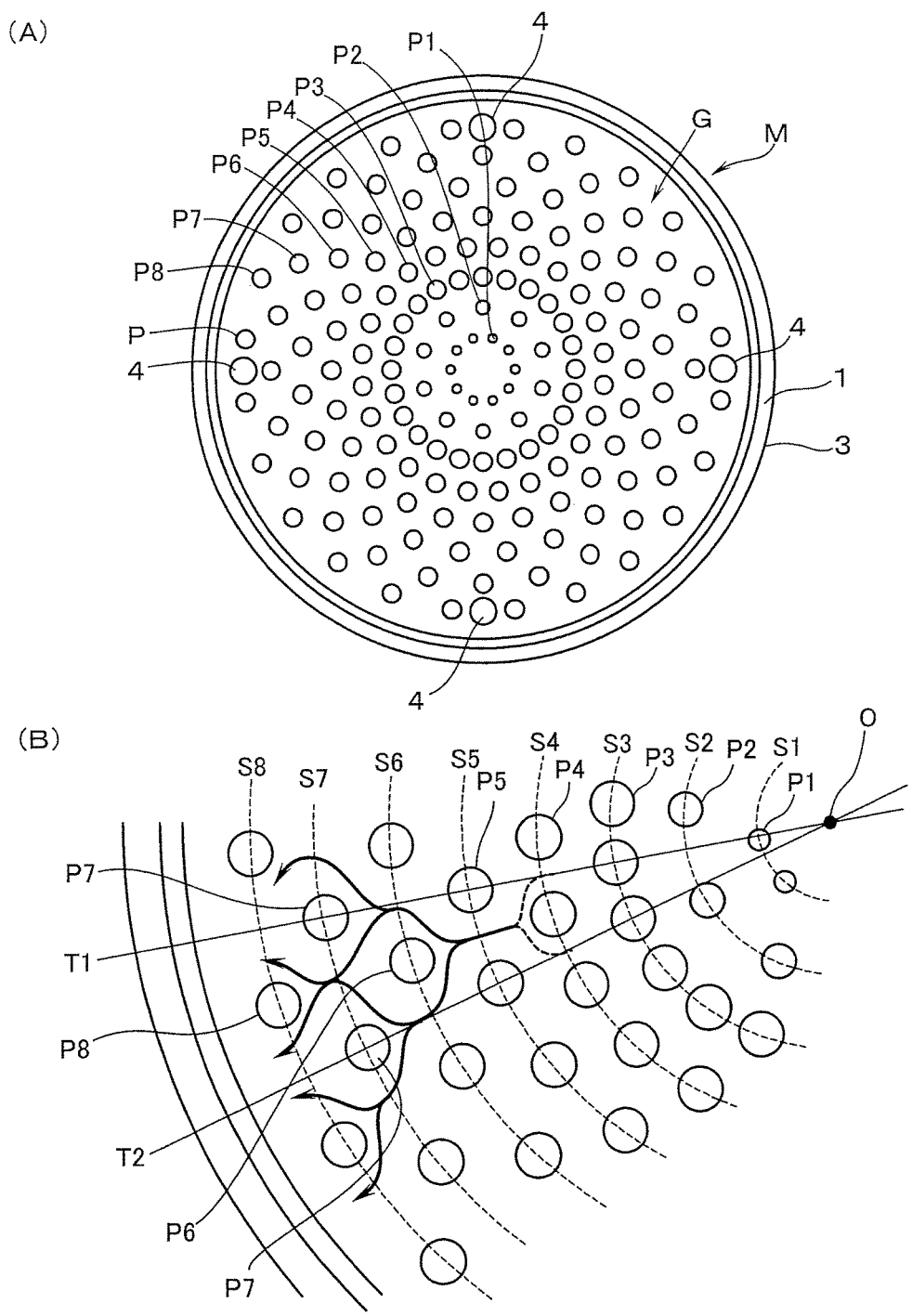
FIG. 4A is a front view illustrating the form of the mixing section of the main body of the mixing device illustrated in FIGS. 1 and 2.
FIG. 4B is a partially enlarged view of FIG. 4A.

Next, an example of the disposition of a large number of pins P1 to P8 formed on the concave portion 2 will be described using FIGS. 4 and 5.

FIG. 4A is a front view illustrating the form of the mixing section of the main body of the mixing device illustrated in FIGS. 1 and 2, and FIG. 4B is a partially enlarged view of FIG. 4A.

A large number of pins P1 to P8 are disposed at equal pitch (circumferential interval) on eight concentric imaginary circles having different diameters.

In the concave portion 2 of the mixing section G, annular rows S1 to S8 (shown in FIG. 4B), each of which is formed by a plurality of pins P disposed on a concentric imaginary circle, are disposed in plural row toward the outer peripheral edge (the outside in the radial direction) from the center of the mixing section G. For this reason, the pins P are disposed in a radial fashion toward the outer peripheral edge from the center of the mixing section G.

Although the details will be described later, ten pins P1 are formed on a pitch circle having the smallest diameter (a pitch circle that is closest to the center point O). Further, twenty-four pins P8 are formed on a pitch circle having the largest diameter (a pitch circle that is farthest from the center point O).

A large number of pins P1 to P8 are disposed such that the fluid comes into contact with the pins P1 to P8 at least once, preferably, in a step-by-step manner in a case where the fluid supplied from the opening 21 of the lid section 20 proceeds radially outward from the center O of the concave portion 2 or a case where the fluid proceeds radially inward toward the center O from the through-hole 4 of the outer peripheral edge portion 1 of the concave portion 2.

Specifically, with respect to the disposition of the pins P1 to P8, for example, the following references can be considered. Numerical values which are illustrated below are an example of design for reliably bringing the fluid into contact with the pins P1 to P8, thereby efficiently mixing the fluid, and are not limited thereto.

In FIG. 2, the large number of pins P1 to P8 are disposed on the circumferences of a plurality of (in the illustration, eight) concentric circles.

A diameter D of each of a large number of pins P1 to P8 is expressed by, for example, the following expression.

$$0.004\,R \leq D \leq 0.089\,R$$

With respect to the pin P1 that is closest to the center point O, ten pins are disposed at regular intervals on the circumference of a pitch circle centered on the point O.

A radius dimension φ1 of the pitch circle in which ten pins P1 are disposed on the circumference is expressed by the following expression.

$$0.13\,R \leq \varphi 1 \leq 0.17\,R$$

For example, in a case where R is 45 mm, φ1 is 7 mm. Then, a diameter D1 of the pin P1 is, for example, 2.0 mm.

The pin P2 radially outward adjacent to the pin P1 is disposed by ten pieces at regular intervals on the circumference of a circle (a circle centered on the point O) having a radius dimension φ2 (>φ1) which is expressed by the following expression.

$$0.17\,R \leq \varphi 2 \leq 0.23\,R$$

For example, in a case where R is 45 mm, φ2 is 9 mm. Then, a diameter D2 of the pin P2 is, for example, 2.5 mm.

The pin P3 radially outward adjacent to the pin P2 is disposed by twenty-four pieces at regular intervals on the circumference of a concentric circle centered on the point O and having a radius dimension φ3 (>φ2). The radius dimension φ3 is expressed by the following expression.

$$0.33\,R \leq \varphi 3 \leq 0.38\,R$$

For example, in a case where R is equal to 45 mm, φ3 is 16 mm. Then, a diameter D3 of the pin P3 is, for example, 4.0 mm.

In the first embodiment, the diameters of the pins P4 to P8 which are located at an area further on the outside in the radial direction than the pin P3 are equal to the diameter D3 of the pin P3.

The pin P4 radially outward adjacent to the pin P3 is disposed by twenty-four pieces at regular intervals on the circumference of a concentric circle centered on the point O and having a radius dimension φ4 (>φ3). The radius dimension φ4 is expressed by the following expression.

$$0.44\,R \leq \varphi 4 \leq 0.49\,R$$

For example, in a case where R is 45 mm, φ4 is 21 mm.

The pin P5 radially outward adjacent to the pin P4 is disposed by twenty-four pieces at regular intervals on the circumference of a concentric circle centered on the point O and having a radius dimension φ5 (>φ4). The radius dimension φ5 is expressed by the following expression.

$$0.57\,R \leq \varphi 5 \leq 0.63\,R$$

For example, in a case where R is 45 mm, φ5 is 27 mm.

The pin P6 radially outward adjacent to the pin P5 is disposed by twenty-four pieces at regular intervals on the circumference of a concentric circle centered on the point O and having a radius dimension φ6 (>φ5). The radius dimension φ6 is expressed by the following expression.

$$0.66\,R \leq \varphi 6 \leq 0.72\,R$$

For example, in a case where R is 45 mm, φ6 is 31 mm.

The pin P7 radially outward adjacent to the pin P6 is disposed by twenty-four pieces at regular intervals on the circumference of a concentric circle centered on the point O and having a radius dimension φ7 (>φ6). The radius dimension φ7 is expressed by the following expression.

$$0.8\,R \leq \varphi 7 \leq 0.85\,R$$

For example, in a case where R is 45 mm, φ7 is 37 mm.

The pin P8 disposed on the outside in the radial direction is disposed by twenty-four pieces at regular intervals on the circumference of a concentric circle centered on the point O and having a radius dimension φ8 (>φ7). The radius dimension φ8 is expressed by the following expression.

$$0.91\,R \leq \varphi 8 \leq 0.96\,R$$

For example, in a case where R is 45 mm, φ8 is 42 mm.

Then, in order for the fluid to come into contact with any of the pins P1 to P8 at least once and preferably repeat step-by-step contact with the pins P1 to P8, as illustrated in FIGS. 2, 4A, and 4B, it is preferable that a straight line (a straight line extending in the radial direction or a straight line extending in a radial fashion) that connects the centers of the pins P1 to P8 and the center O of the concave portion 2 be disposed so as not to conform to a straight line that connects the centers of the pins radially inward adjacent to the pins P1 to P8 and the center O of the concave portion 2.

That is, it is preferable that the centers of the pins P1 to P8 and the centers of the pins radially inward adjacent to the pins P1 to P8 be disposed so as to be deviated from each other (be out of alignment) in the circumferential direction of the concave portion 2. For example, in FIGS. 2, 4A, and 4B, the center of the pin P5 and the center of the pin P4 radially inward adjacent to the pin P5 are deviated from each other (be out of alignment) in the circumferential direction of the concave portion 2. For this reason, a straight line that connects the center of the pin P5 and the center O and a straight line that connects the center of the pin P4 and the center O do not conform to each other.

Further, in other words, as illustrated in FIG. 4B, for example, taking the pins of the annular rows S6 to S8 as an example, it is preferable that at least the pins P6 and P8 of the other annular rows S6 and S8 adjacent to the annular row S7 in the radial direction of the mixing section G be disposed at an area surrounded by two straight lines T1 and T2 that connect the centers of two adjacent pins P7 of a plurality of pins P7 in the annular row S7 and the center of the mixing section G. In the flow path (the concave portion 2), such pin arrays are continuously formed.

For example, due to such pin disposition, as schematically illustrated by arrows in FIG. 4B, the fluid supplied by being pressurized to a predetermined pressure (for example, 0.1 MPa) or more by the pressurizing means passes between adjacent pins in the annular row (for example, S6) with the contact with the pins and comes into contact with the pins of the other adjacent annular row (for example, S7). Then, the fluid passes between adjacent pins again and comes into contact with the pins of the other adjacent annular row (for example, S8). In this manner, the fluid passes through the flow path while repeating the contact with the protruding pins in the flow path (the concave portion 2) between the vicinity of the center (the vicinity of the supply hole) of the mixing section and the vicinity of the outer peripheral edge (the vicinity of the discharge hole), and at this time, the plurality of pins P vibrates in ultrasonic waves due to collision with the fluid. Then, the ultrasonic vibration of the pin P causes cavitation in the fluid, and due to the cavitation, the substances to be mixed are effectively and homogeneously decentralized, and thus mixing is promoted.

In addition, the pin disposition illustrated in FIGS. 1, 2, 3, 4A, and 4B is an example in which the pins "are disposed such that in a case where the fluid proceeds radially outward from the center O of the concave portion 2, or a case where the fluid proceeds radially inward toward the center O from the outer peripheral edge portion 1 of the concave portion 2, the fluid comes into contact with the pins P at least once, preferably, in a step-by-step manner". In other words, even in pin disposition other than that illustrated in FIGS. 1, 2, 3, 4A, and 4B, it is possible to dispose the pins "such that in a case where the fluid proceeds radially outward from the center O of the concave portion 2, or a case where the fluid proceeds radially inward toward the center O from the outer peripheral edge portion 1 of the concave portion 2, the fluid comes into contact with the pins P at least once, preferably, in a step-by-step manner".

Figure 5:
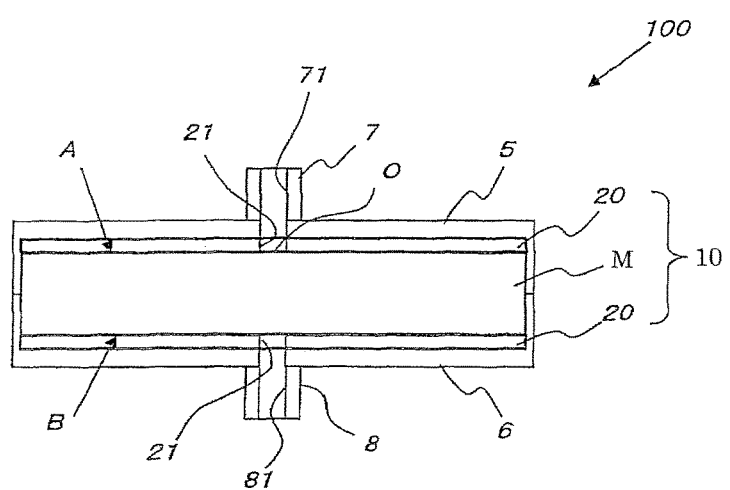
FIG. 5 is an explanatory diagram illustrating an embodiment of the mixing device according to the invention and schematically shows the principle of mixing.

A mixture fluid production device 100 shown in FIG. 5 is configured by accommodating the mixing device 10 (the main body M and the lid sections 20) in casings 5 (a casing on the supply side) and 6 (a casing on the discharge side). The casing on the supply side 5 and the casing on the discharge side 6 are connected so as to maintain airtightness by known means.

A supply pipe 7 is provided at the casing on the supply side 5, and a discharge pipe 8 is provided at the casing on the discharge side 6.

The supply pipe 7 communicates with the opening 21 of the lid section 20 on the supply side (in FIG. 5, the upper lid section) through a first penetration portion 71. The first penetration portion 71 is also formed in the casing on the supply side 5 in which the supply pipe 7 is provided.

The discharge pipe 8 communicates with the opening 21 of the lid section 20 on the discharge side (in FIG. 5, the lower lid section) through a second penetration portion 81. The second penetration portion 81 is also formed in the casing on the discharge side 6 in which the discharge pipe 8 is provided.

In the mixture fluid production device 100 shown in FIG. 5, a fluid (mixed flow) that includes materials such as a solid, a gas, and a liquid-phase fluid (a solvent) to be mixed flows into an area in the vicinity of the center point O of the concave portion 2 on the front side (the concave portion 2 on the upper side in FIG. 3; in FIG. 5, denoted by sign A) shown in FIGS. 1 and 2 through the supply pipe 7, the first penetration portion 71, and the opening 21 (the supply hole) of the lid section 20.

The mixed flow flowed in flows toward the outside in the radial direction of the concave portion 2. However, at this time, the mixed flow comes into contact with the plurality of pins P1 to P8, whereby the solid, the gas, or the like is homogeneously dispersed in the liquid-phase fluid, and thus mixing is promoted.

The mixed flow which has flowed radially outward flows to the radially outer edge portion of the concave portion 2 on the back side (the concave portion 2 on the lower side in FIG. 3; in FIG. 5, denoted by sign B) which is not shown in FIGS. 1 and 2, through the through-hole 4 (the discharge hole or the supply hole) of the concave portion 2 illustrated in FIG. 2.

The mixed flow which has flowed to the outer edge portion 1 side of the concave portion 2 on the back side flows radially inward toward the center O in the concave portion 2. Also at this time, a solute (the solid, the gas, or the liquid-phase fluid) in the mixed material comes into contact with a large number of pins P1 to P8, thereby being efficiently mixed.

The mixed flow which has reached the center O of the concave portion 2 on the back side is in a state where the liquid-phase fluid and a desired solid, gas, or the like are mixed with each other, and is discharged from the discharge pipe 8 through the opening 21 (the discharge hole or the supply hole) of the lid section 20 which covers the concave portion 2 on the back side, and the second penetration portion 81, thereby being sent to, for example, a storage unit (not shown).

In FIG. 5, the mixing device 10 is in a state of being accommodated such that the lid sections 20 come into close contact with the front and back surfaces (both upper and lower end faces) of the main body M. The pressurizing means (a compressor) (not shown) is included in the mixture fluid production device 100, and the fluid having high pressure is pumped by the pressurizing means.

FIG. 5 shows a one-module mixing device 10 configured to include a single main body M and two lid sections 20. However, also in the one-module mixing device 10, the contact and the dispersion effect of the fluid are efficiently performed.

In FIG. 5, a single mixing device 10 is accommodated in the casings 5 and 6. However, in a mixture fluid production device 100A of FIG. 6, two mixing devices 10A and 10B are accommodated in a casing 56.

Figure 6:
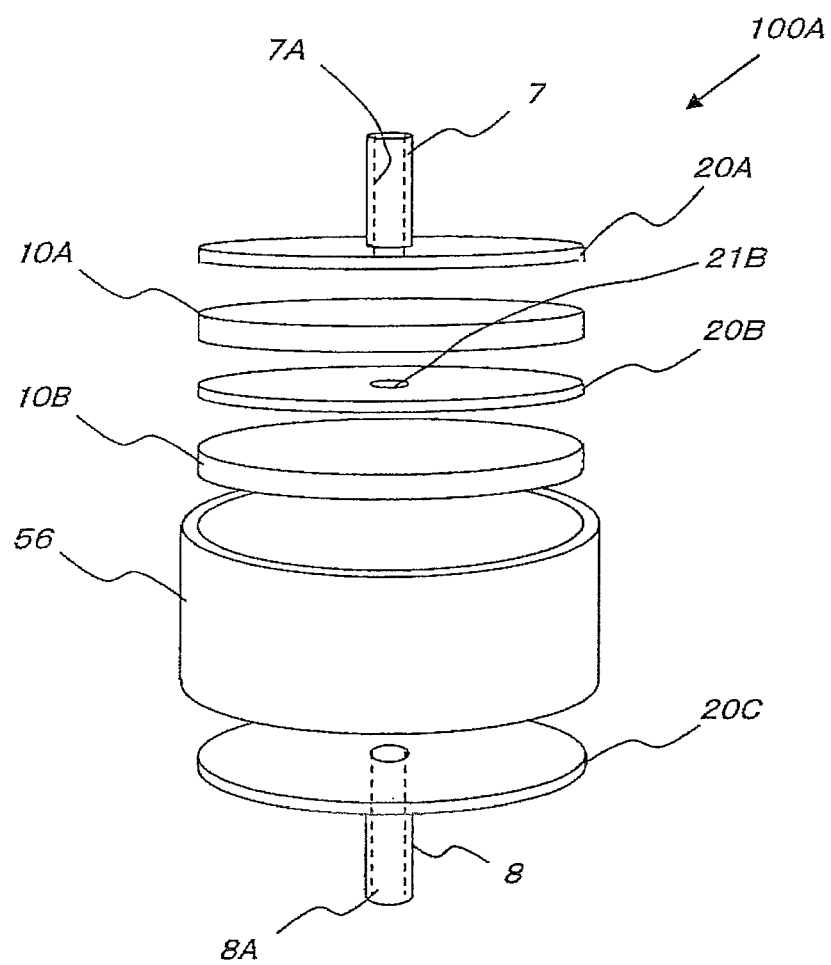
FIG. 6 is an assembly diagram illustrating an embodiment of the mixing device according to the invention.

In FIG. 6, in order to clarify the flow of the fluid (the mixed flow) which includes materials to be mixed, the supply pipe 7, the discharge pipe 8, and the casing 56 are shown separately.

The supply pipe 7 is integrally connected to a first lid section 20A at the center of a surface (an upper surface of illustration) on one side in the first lid section 20A.

A through-hole (a supply hole) 7A penetrating from an end portion of the supply pipe 7 to a surface (a lower surface of illustration) on the other side in the first lid section 20A is provided.

The discharge pipe 8 is integrally connected to a third lid section 20C at the center of a surface (an upper surface of illustration) on one side in the third lid section 20C.

A through-hole (a discharge hole) 8A penetrating from an end portion of the discharge pipe 8 to a surface (a lower surface of illustration) on the other side in the third lid section 20C is provided.

Each of the mixing devices 10A and 10B has the mixing sections on the front surface side and the back surface side of the central portion, as illustrated in FIGS. 1 and 2.

As illustrated in FIG. 6, the fluid which includes materials to be mixed flows to the center of the concave portion (illustration is omitted) of the mixing section on the front surface side of the mixing device 10A through the supply pipe 7 and the through-hole (the supply hole) 7A of the first lid section 20A. Then, the fluid comes into contact with the pins P (illustration is omitted) when moving radially outward from the center of the concave portion, and thus mixing of the solid, the gas, or the like with the liquid-phase fluid is promoted. The mixed flow which has mixed is discharged from the through-hole (illustration is omitted) which is located at the radially outer edge portion of the concave portion (illustration is omitted), and also supplied to the outer peripheral edge portion (illustration is omitted) of the concave portion of the mixing section (for example, the mixing section on a side which is not shown FIGS. 1 and 2) on the back surface side (the lower side) of the first mixing device 10A. Therefore, in this case, the through-hole functions as the discharge hole for the fluid and on the other hand, also functions as the supply hole for the fluid. Then, the fluid flows radially inward in the concave portion and comes into contact with the pins P, and thus mixing of the solid, the gas, or the like with the liquid-phase fluid is further promoted.

The fluid (the mixed flow) which has reached the central portion of the concave portion (illustration is omitted) of the mixing section on the back surface side (the lower side) in the first mixing device 10A is supplied to the center of the concave portion (illustration is omitted) of the mixing section on the front surface side (the upper side) in the second mixing device 20B through an opening (a supply hole) 21B of a second lid section 20B. When the fluid flows radially outward from the center of the concave portion, the fluid comes into contact with the pins P (in FIG. 6, not shown), and thus mixing of the solid, the gas, or the like with the liquid-phase fluid is promoted. Then, the mixed fluid (the mixed flow) is supplied from the radially outer edge portion (illustration is omitted) of the concave portion to the outer peripheral edge portion (illustration is omitted) of the concave portion of the mixing section on the back surface side (the lower side) of the second mixing device 10B. In addition, the mixed fluid (the mixed flow) flows radially inward in the concave portion and comes into contact with the pins P, and thus mixing of the solid, the gas, or the like with the liquid-phase fluid is further promoted.

The fluid (the mixed flow) which has reached the central portion of the concave portion (illustration is omitted) of the mixing section on the back surface side (the lower side) in the second mixing device 10B passes through the discharge pipe 8 through the through-hole 8A of the third lid section 20C.

Figure 7:
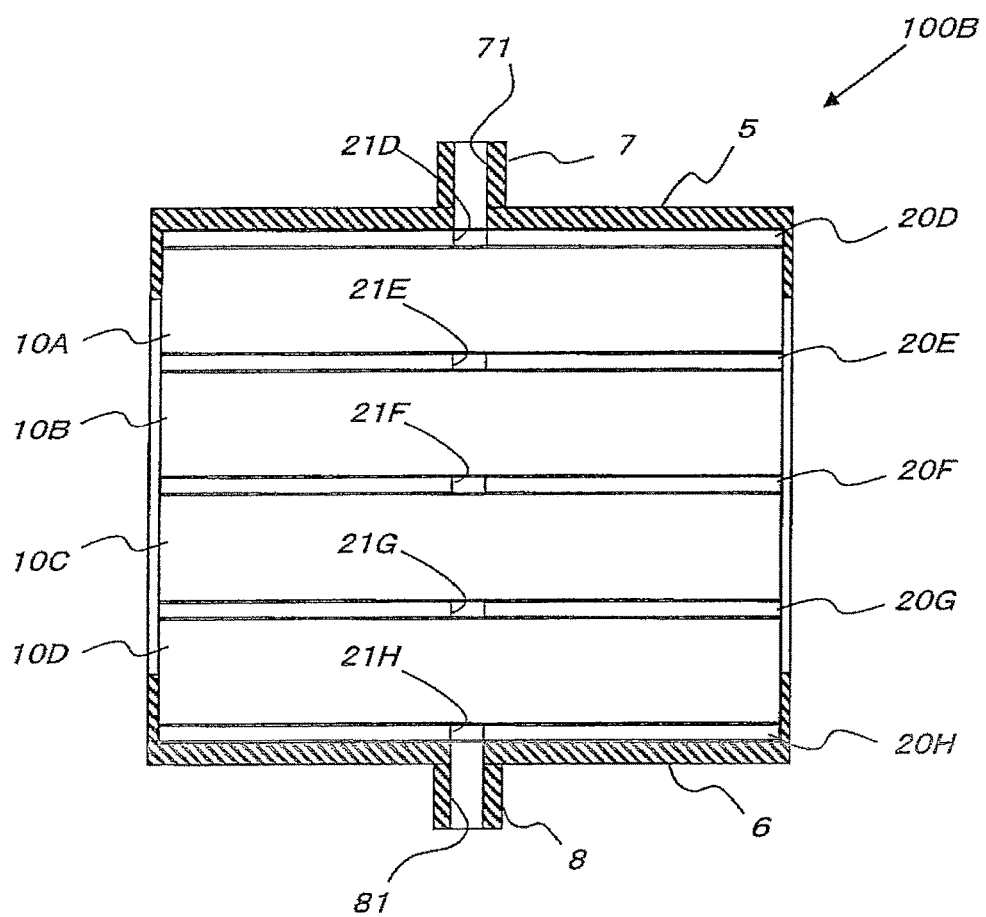
FIG. 7 is an assembly diagram illustrating an embodiment of the mixing device according to the invention.

In a mixture fluid production device 100B illustrated in FIG. 7, mixing devices 10A to 10D of a larger number of stages (four stages) are accommodated in a casing.

In FIG. 7, the fluid which includes materials to be mixed, supplied through the supply pipe 7, is discharged from the discharge pipe 8 by way of an opening 21D of a first lid section 20D, the mixing sections of the front and back (a side shown in FIGS. 1 and 2 and a side not shown) of the first mixing device 10A, an opening 21E of a second lid section 20E, the mixing sections of the front and back in the second mixing device 10B, an opening 21F of a third lid section 20F, the mixing sections of the front and back in the third mixing device 10C, an opening 21G of a fourth lid section 20G, the mixing sections of the front and back in the fourth mixing device 10D, and an opening 21H of a fifth lid section 20H.

Then, when the fluid passes through the mixing sections of the front and back in the first to fourth mixing devices 10A to 10D, the fluid and the pins P continuously come into contact with each other in each mixing section, and thus mixing of the solid, the gas, or the like with the liquid-phase fluid is reliably and efficiently performed. The first to fourth mixing devices 10A to 10D are successively provided, thereby enabling more efficient mixing.

According to the experiment by the inventor, in the mixture fluid production device according to the invention, by the mixing device of a single stage having a diameter of 3 cm, it was possible to pulverize and mix a material to a level which needs a path length of 3 m in a static mixer of the related art.

Figure 8:
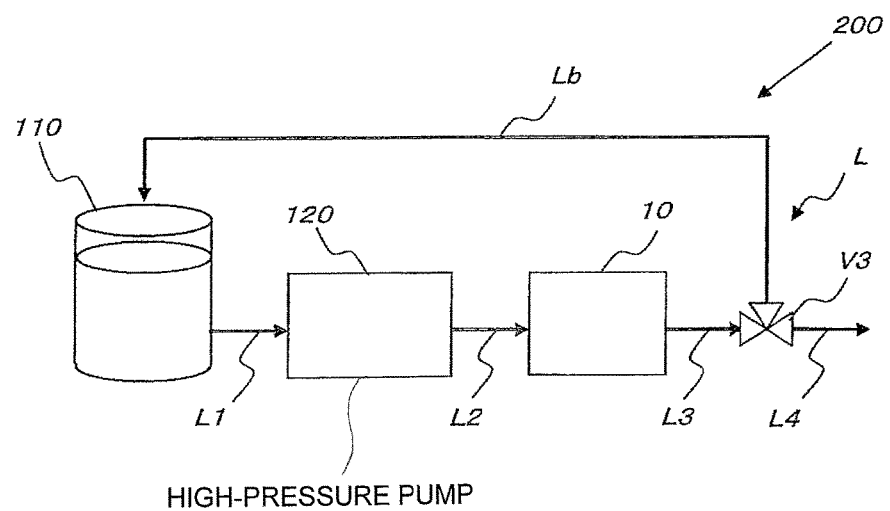
FIG. 8 is a block diagram illustrating an embodiment of a mixture fluid production device using the mixing device according to the invention.

FIG. 8 is a schematic diagram illustrating an embodiment of the mixture fluid production device according to the invention.

A mixture fluid production device 200 has the mixing device 10, a material storage tank 110, a high-pressure pump (pressurizing means) 120, a material transport line L in which a three-way valve V3 is interposed.

The material transport line L includes a line L1, a line L2, a line L3, a line L4, and a return line Lb.

The line L1 connects the material storage tank 110 and the high-pressure pump 120, the line L2 connects the high-pressure pump 120 and the mixing device 10, and the line L3 connects the mixing device 10 and the three-way valve V3. Further, the line L3 is branched into the line L4 and the return line Lb at the three-way valve V3.

The three-way valve V3 makes the line L3 and the line L4 communicate with each other in a case of supplying a material mixed in the mixing device 10 to a supply destination (the next step). On the other hand, in a case of wishing to temporarily stop the supply of the material, the three-way valve V3 makes the line L3 and the return line Lb communicate with each other, thereby returning the mixed flow discharged from the mixing device 10 to the material storage tank 110, whereby it is possible to circulate the mixed flow.

A plurality of materials to be mixed (dispersed, emulsified, solubilized, or the like) is stored in the material storage tank 110.

The material storage tank 110 stores two or more kinds of various materials (a solid-a liquid, a liquid-a liquid, a gas-a liquid, or the like) that are step objects. At a stage where the materials are stored in the material storage tank 110, the materials to be mixed may be completely separated.

In the mixture fluid production device 200, the discharge pressure of the high-pressure pump 120 can be set to be greater than or equal to 0.1 MPa.

In the experiment by the inventor, it is confirmed that if a composite material is supplied to the supply pipe 7 of the mixing device 10 at pressure of greater than or equal to 0.1 MPa, mixing (dispersion, solubilization, emulsification, or the like) is sufficiently performed.

Further, according to the measurement by the inventor, it is found that pressure loss of the mixing device 10 is suppressed to a range of about 10% to about 20% of the discharge pressure of the high-pressure pump 120.

The mixture fluid production device 200 can include a cooling device or the like. The pin of the mixing section of the mixing device 10 ultra-vibrates with the contact with the fluid supplied by the high-pressure pump 120, thereby being able to generate cavitation of the fluid. In this way, the materials to be mixed in the fluid are homogeneously decentralized, thereby being dissolved, dispersed, or the like in the liquid-phase fluid. At this time, in a case where the mixed flow is heated due to the cavitation, cooling treatment by the cooling device can be performed. As the cooling device, for example, a water tank or the like for performing cooling by immersing (so-called "dipping") the mixing device 10 as a whole in a water tank or the like can be exemplified.

Figure 9:
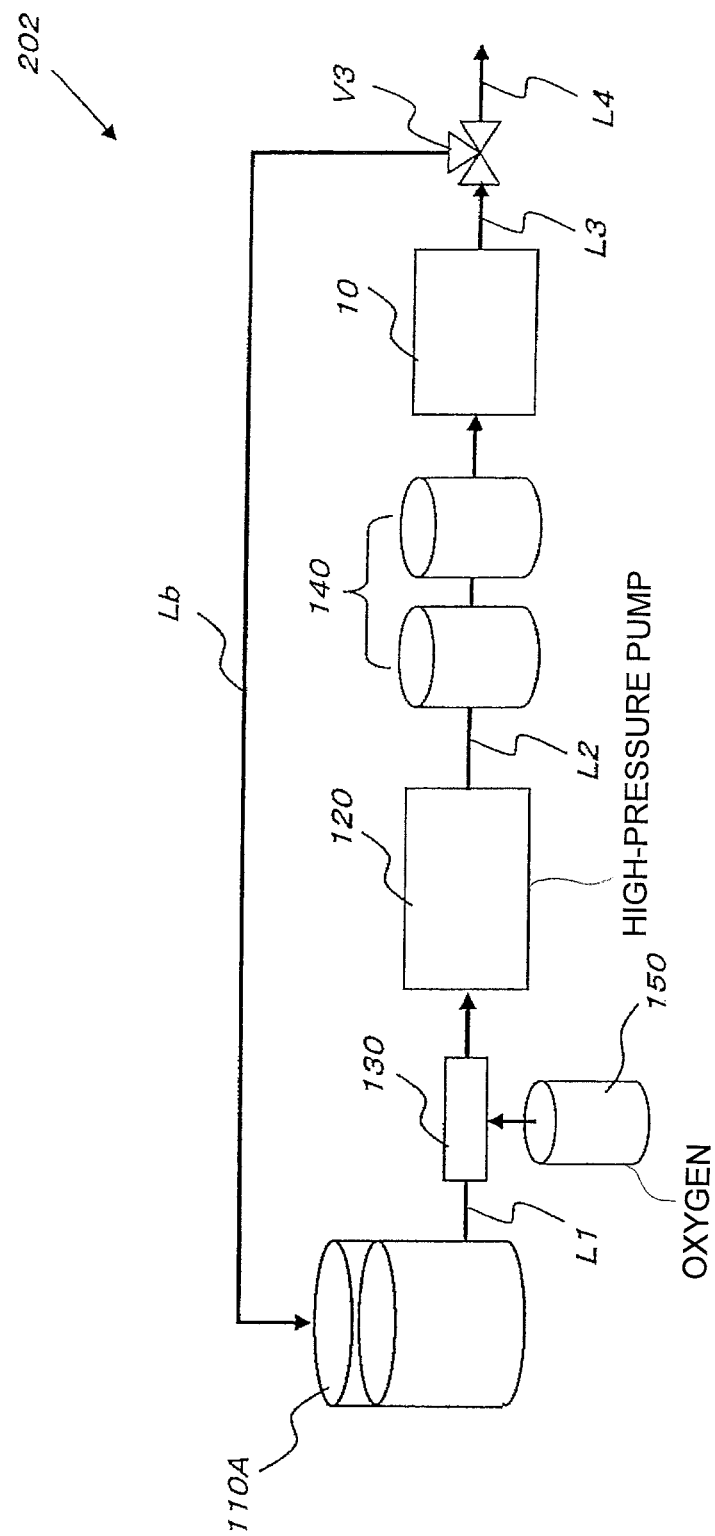
FIG. 9 is a block diagram illustrating an embodiment of the mixture fluid production device using the mixing device according to the invention.

FIG. 9 is a schematic diagram illustrating the configuration of a mixture fluid production device 202 according to the invention.

In the mixture fluid production device 202 of FIG. 9, with respect to the mixture fluid production device 200 of FIG. 8, the material storage tank 110 is replaced with a water storage tank 110A, a gas-liquid mixing device 130 is disposed in the line L1, and a gas-liquid mixing rate adjustment mechanism 140 is disposed in the Line 2.

Here, as for the gas-liquid mixing device 130, a gas-liquid mixing device of a type to draw in oxygen by using negative pressure of the line L1 is used. Here, if water from the water storage tank is mixed with oxygen by increasing pressure on the oxygen side, there is a case where the high-pressure pump is damaged. In contrast, in the experiment by the inventor, it is confirmed that if the gas-liquid mixing device 130 of a type (a type shown in FIG. 9) to draw in oxygen by using negative pressure is used, the possibility of the high-pressure pump 120 being damaged becomes very low.

The gas-liquid mixing device 130 is connected to an oxygen container 150 and suctions oxygen in the oxygen container 150 into the line L1 by using the negative pressure of the line L1 (since the fluid is suctioned by the high-pressure pump 120, negative pressure is generated in the line L1).

In the mixture fluid production device 202, oxygen and water flow through the mixing device 10, whereby the water containing oxygen collides with the pins P, and thus oxygen is uniformly dispersed and solubilized in the water. As a result, the amount of dissolved oxygen in the water becomes very high. Specifically, it is possible to produce water which can maintain a state where the dilute concentration of dissolved oxygen is greater than or equal to 25 ppm, preferably, greater than or equal to 35 ppm, for a long period of time (for example, 35 days or more).

Further, in the mixture fluid production device 202, if, for example, a cooling water storage tank (not shown) is connected to the line L4, it is possible to produce water in which oxygen and water are uniformly mixed by the mixing device 10 and the amount of dissolved oxygen is large in the cooling water storage tank.

The gas-liquid mixing rate adjustment mechanism 140 is a mechanism for suppressing pulsation in the line L2 or later and a mechanism to adjust a mixing rate of a gas and a liquid.

In order to produce water with high level of dissolved oxygen, it is desirable to maintain a constant gas-liquid mixing rate at the stage just before supply to the mixing device 10. However, if pulsation occurs in a water circulation system, it becomes difficult to make a gas-liquid mixing rate constant.

Even if pulsation occurs in a water circulation system of the mixture fluid production device of FIG. 9, the pulsation is suppressed by providing the gas-liquid mixing rate adjustment mechanism 140, and thus a mixing rate of a gas and a liquid can be maintained constant.

As for the gas-liquid mixing rate adjustment mechanism 140, in the example shown in the drawing, two containers are used. However, a single container is also acceptable. Further, the shape of the container is not limited to a cylindrical shape.

Although illustration is omitted, it is also possible to omit disposition of the gas-liquid mixing device 130 in the line L1 and connect the oxygen container 150 to the line L2 (the discharge side of the high-pressure pump) by an oxygen supply line.

In this case, in order to mix oxygen into the line L2, high pressure greater than or equal to the discharge pressure of the high-pressure pump 120 is required.

In the mixture fluid production device 202 of FIG. 9, by switching the three-way valve V3, it is possible to return the mixed flow discharged from the mixing device 10 to the water storage tank 110A by the line Lb, thereby circulating the mixed flow. Alternatively, it is possible to discharge water with oxygen dissolved therein to the next step as it is, without circulating the water with oxygen dissolved therein.

Next, an example of a production method of oxygen-containing ice will be described with reference to FIG. 10.

Figure 10:
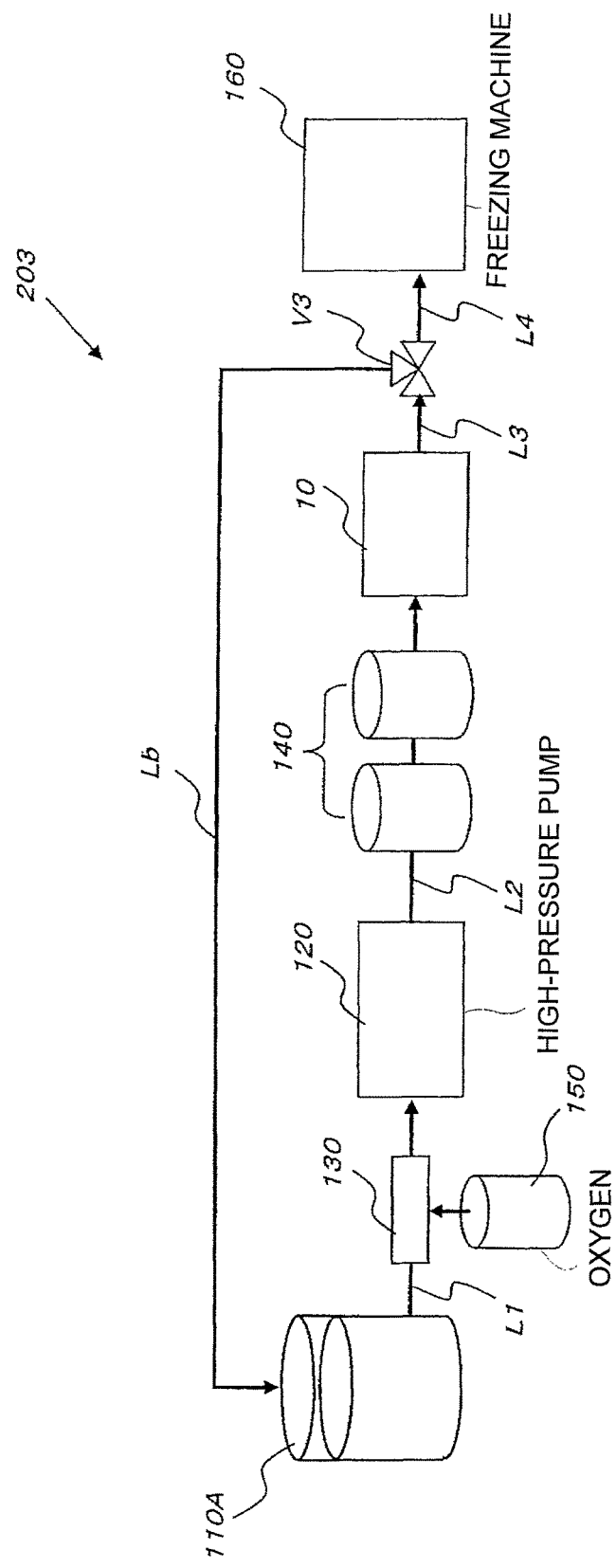
FIG. 10 is a block diagram illustrating an embodiment of the mixture fluid production device using the mixing device according to the invention.

A system (the entire mixing system is denoted by reference numeral 203) of producing ice with high oxygen content by using water produced in the mixture fluid production device 202 of FIG. 9 is shown in FIG. 10.

In a mixture fluid production device 203 of FIG. 10, the line L4 of the mixing system 202 of FIG. 9 is connected to a freezing machine 160.

The mixture fluid production device 203 of FIG. 10 is configured so as to produce ice with high oxygen content by freezing the mixed flow (water mixed with oxygen) discharged from the mixing device 10 by the freezing machine 160.

As for the freezing machine, a known and commercially available freezing machine can be applied.

The ice (ice which includes a large amount of oxygen) produced by the mixture fluid production device 203 of FIG. 10 generates a large amount of oxygen when being dissolved. For this reason, if the ice is used when transporting a squid, an octopus, or a shellfish, it is possible to maintain low temperature by heat of condensation when the ice is dissolved, and also it is possible to promote cutaneous respiration of the squid, the octopus, or the shellfish because a large amount of oxygen is generated. As a result, it is possible to preserve the freshness of the squid, the octopus, or the shellfish which is transported.

Here, in the experiment by the inventor or the like, in the oxygen-containing ice produced by the mixture fluid production device 203 of FIG. 10 and having a size of length 30 mm, width 30 mm, and height 25 mm, compared to normal ice of the same size, which is ice-made in a household refrigerator, time to dissolve is longer by ten minutes or more at atmospheric temperature of 20° C. and in the air. That is, if the ice produced by the mixture fluid production device 203 of FIG. 10 is used, it is possible to supply oxygen and also suppress a change in temperature (an increase in temperature). For this reason, when transporting a fresh flower, a pot flower, or vegetables, it is possible to reduce a change in temperature and preserve freshness by oxygen which is generated when the ice is dissolved.

Similarly, if the configuration of the mixture fluid production device 203 of FIG. 10 is applied to a large-scaled ice-maker which is provided in a market or a fishing boat, it is possible to provide a function to reduce a change in temperature and produce ice which generates oxygen when being dissolved, in large amounts. In this way, it becomes possible to perform work such as storage, preservation, or transportation while preserving the freshness of fresh food, a flower, vegetables, or the others by using the ice with a large amount of oxygen included inside.

In addition, if the ice with a large amount of oxygen included therein is supplied into the soil in a high-temperature area, it is possible to reduce the temperature of the soil in the high-temperature area and also supply oxygen into the soil.

Alternatively, if the ice with a large amount of oxygen included therein is put into the sea, it is possible to suppress an increase in the temperature of seawater of a sea area with the ice put therein, and it becomes possible to supply oxygen into seawater in the sea area.

The invention is not limited to the embodiment described above. For example, the large number of pins provided in the mixing device need not be disposed on the respective circumferences of a plurality of concentric circles. Further, it is possible to adopt various forms according to the radius dimension of the concentric circle, the diameter of the pin, the number of pins, a use of the mixing device, the materials to be mixed, or the like. Further, in the mixture fluid production device, it is possible to appropriately design the number of mixing devices which are used, the disposition of the mixing device, or the like.

EXAMPLES

Figure 15:
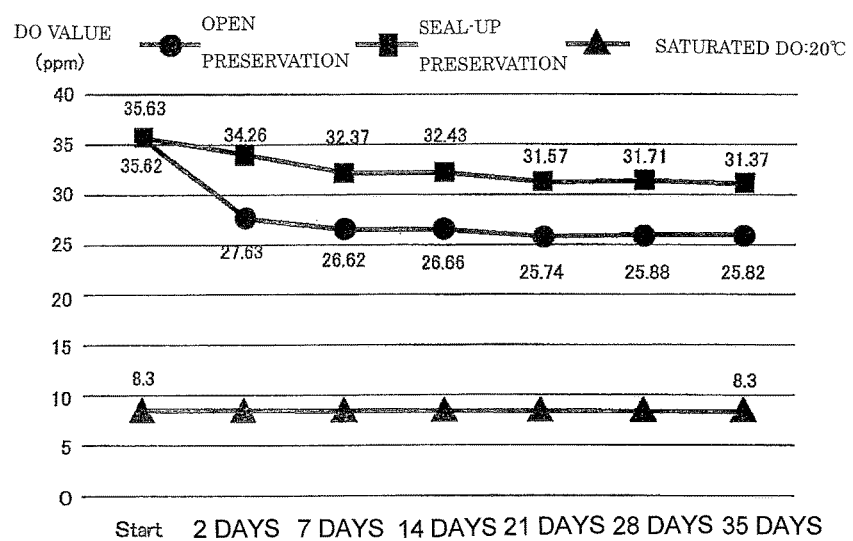
FIG. 15 is a graph showing variations with times of dissolved oxygen concentrations of oxygen-containing water produced by the mixture fluid production device according to the invention.
Figure 16:
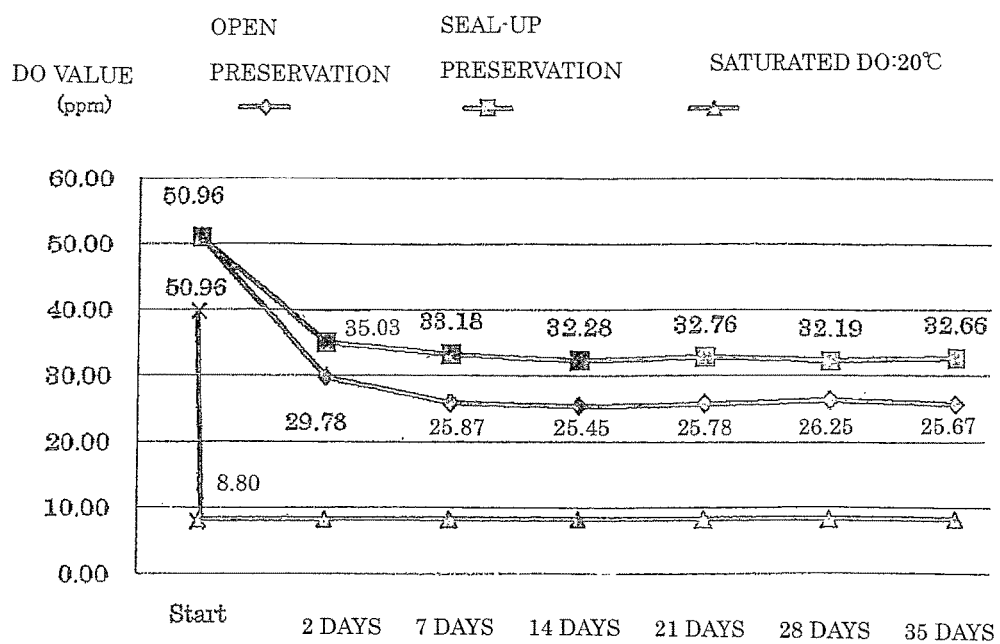
FIG. 16 is a graph showing variations with times of dissolved oxygen concentrations of oxygen-containing water produced by the mixture fluid production device according to the invention.

The operation and effects of the mixture fluid production device 202 schematically shown in FIG. 9 are shown in FIGS. 15 and 16 showing the experimental results by the inventor.

Specifically, oxygen-containing water was produced by the mixture fluid production device 202 which uses the mixing device 10 shown in FIGS. 11 to 14 and is shown in FIG. 9.

The basic configuration of the mixing device 10 is based on the configuration of the mixing device illustrated in FIGS. 1 and 2 or the like. However, the number of pins P of the mixing section G, the disposition of the pins P, or the like is designed in a form suitable for this example.

Figure 11:
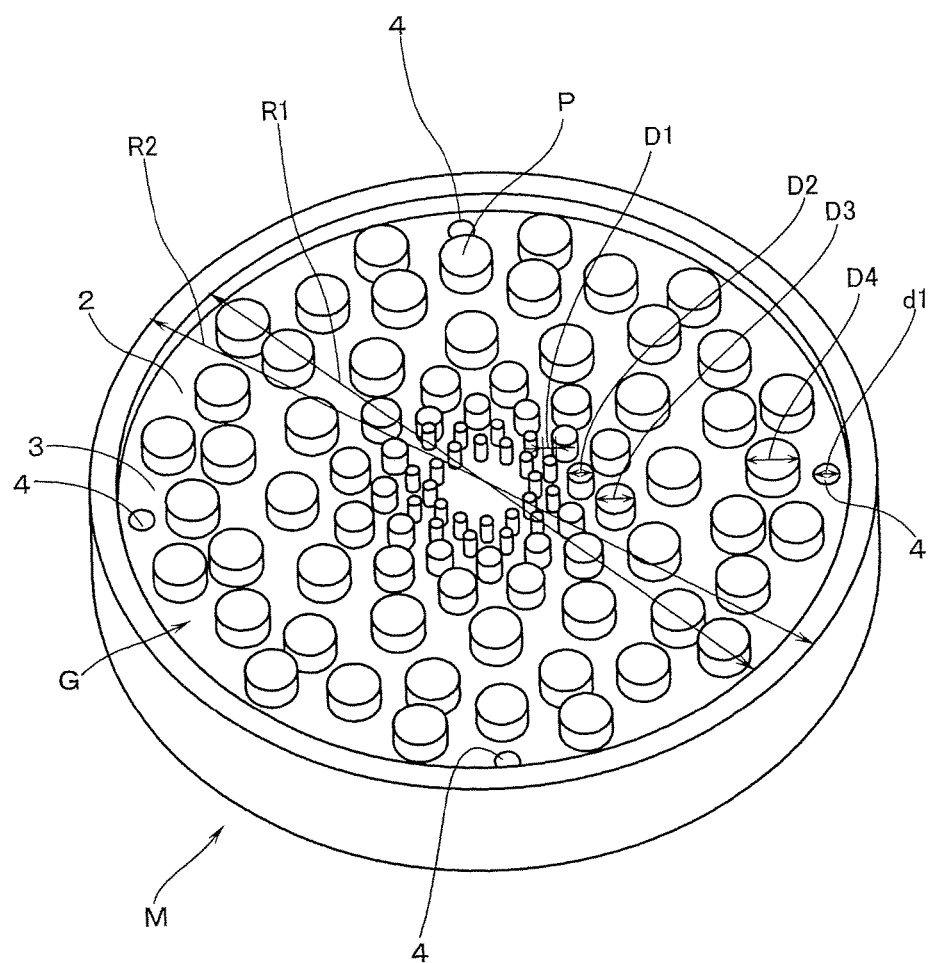
FIG. 11 is a perspective view schematically showing the form of the main body of the mixing device used in an example.
Figure 12:
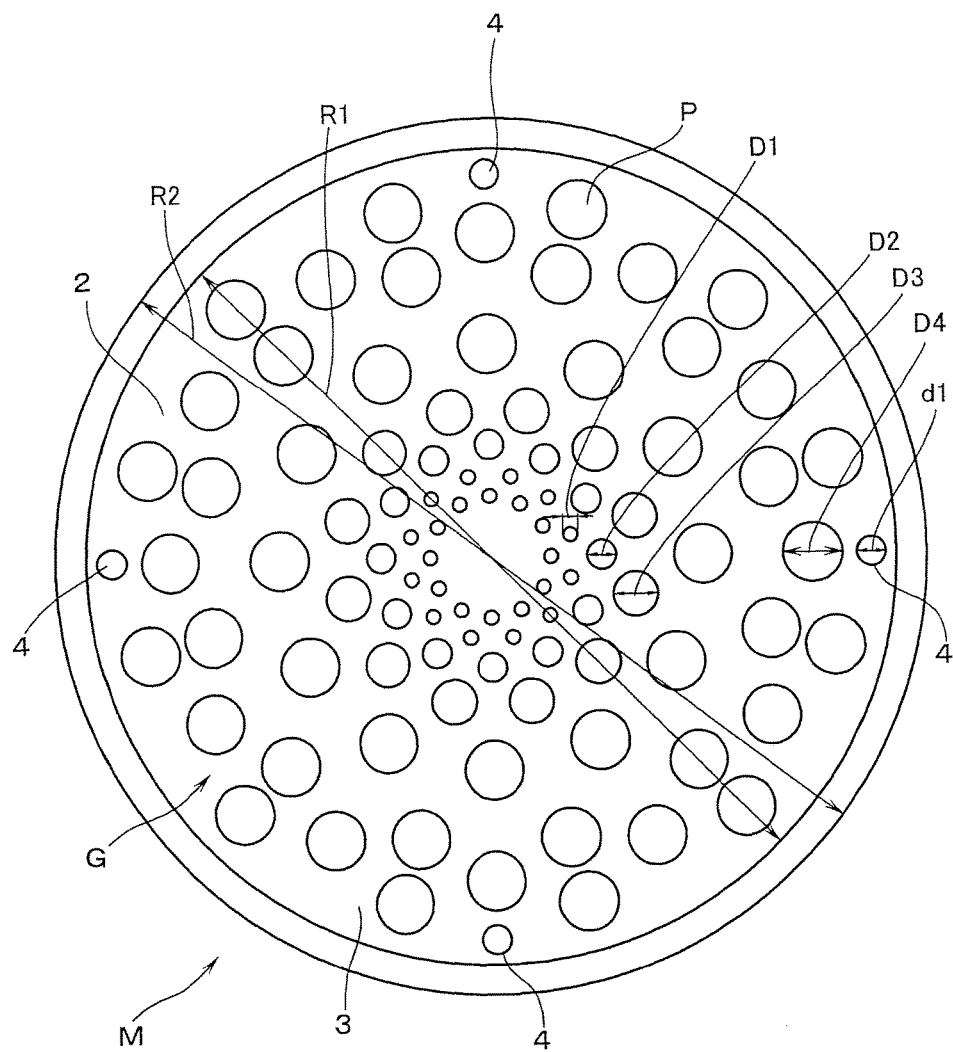
FIG. 12 is a front view schematically showing the form of the main body of the mixing device used in the example.

In the mixing device used in the example, as shown in FIGS. 11 and 12, an inner diameter R1 of the disk-shaped main body M is designed to 28.0 mm and an outer diameter R2 is designed to 30.0 mm. Further, a thickness W (shown in FIG. 13) of the main body M (the thickness of a portion other than the concave portion) is designed to 5.0 mm.

Figure 13:
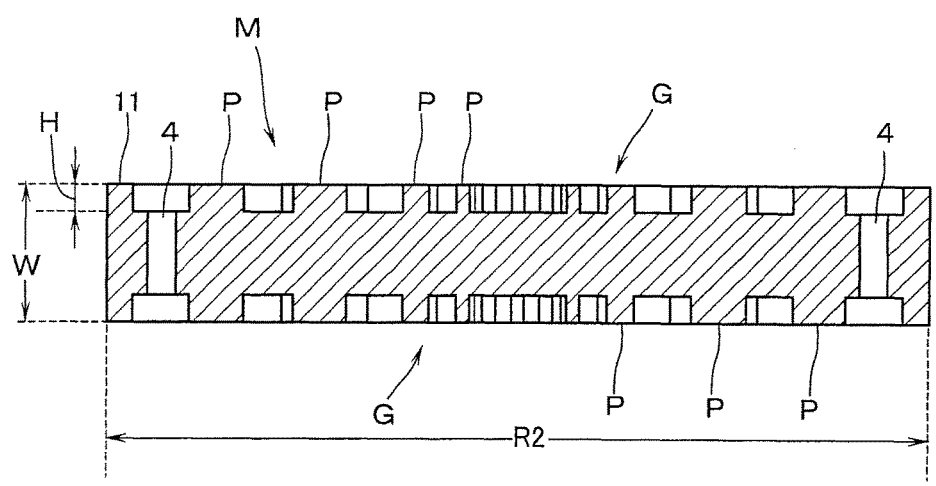
FIG. 13 is a cross-sectional view schematically showing the form of the main body of the mixing device used in the example.

As shown in FIGS. 11 to 13, the pins P protrude from the front and back surfaces of the concave portion 2 (the central portion 3), and thus the mixing sections G are formed (the sign of the pin P is given to only some of the pins and the signs of the other pins are omitted for convenience). Specifically, the pin P has a columnar shape, and the annular row (a sign is omitted, refer to FIG. 4B or the like) formed by disposing twelve pins P on an imaginary circle is disposed by eight rows in a direction of the outer peripheral edge of the mixing section G from the center of the concave portion 2 of the mixing section G. The diameter D1 of each of the pins P of the first and second annular rows on the outside from the center of the concave portion 2 of the mixing section G is designed to 0.5 mm. The diameter D2 of each of the pins P of the third annular row on the outside thereof is designed to 1.0 mm. The diameter D3 of each of the pins P of the fourth annular row on further the outside is designed to 1.5 mm. A diameter D4 of each of the pins P of the fifth to eighth annular rows on further the outside is designed to 2.0 mm. Further, in any of the pins P, a height H (shown in FIG. 13) thereof is designed to 1.0 mm and conforms to the height of an outer peripheral wall portion 11 (shown in FIG. 13) of the mixing section G.

A diameter d1 of each of the through-holes 4 (the discharge hole or the supply hole) formed at four places in the vicinity of the outer peripheral edge of the mixing section G is designed to 1.0 mm.

Figure 14:
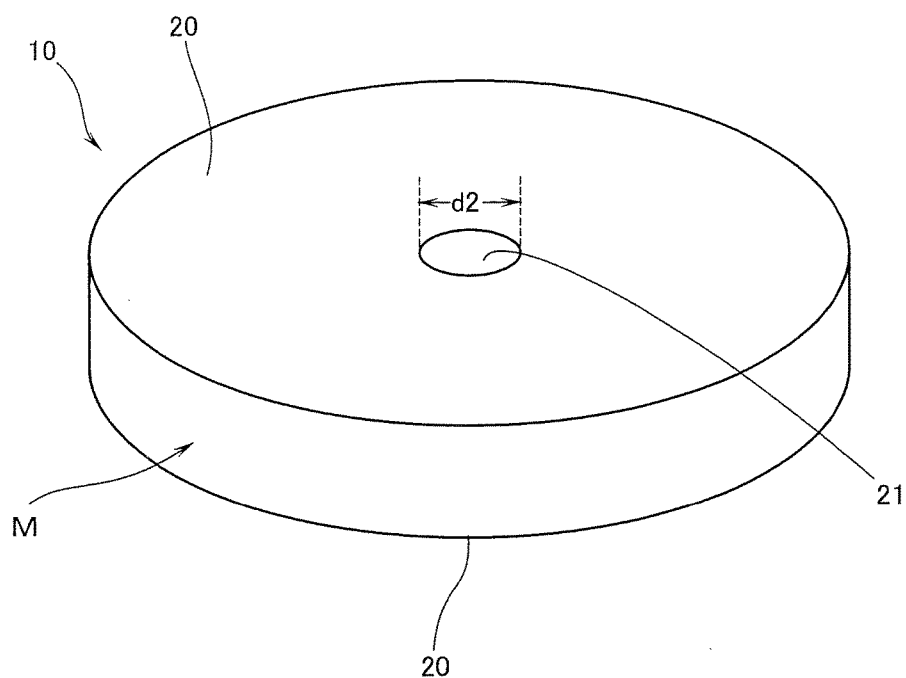
FIG. 14 is a perspective view schematically showing the form of the mixing device used in the example.

In addition, FIG. 14 is a perspective view showing the mixing device 10 formed by fitting the lid sections 20 to the mixing sections G of the front and back surfaces (the top and bottom) of the main body M. The diameter of the lid section 20 is designed to 30.0 mm, similar to the mixing section G. Further, the opening 21 (the supply hole or the discharge hole) having a circular shape is formed at the center of the lid section 20 and a diameter d2 of the opening 21 is designed to 4.0 mm.

A mixture fluid production device (refer to FIG. 9) was configured by disposing the mixing device 10 designed as described above, to overlap in two stages up and down by the same method as that illustrated in FIG. 7, and further providing the pressurizing means (the high-pressure pump), the gas-liquid mixing device, and the like.

In the mixture fluid production device, oxygen-containing water was produced by supplying about 10 L of pure water and oxygen (pure oxygen of about 1.0 L/min) into the mixing device at pressure of 0.3 Mpa by the high-pressure pump as the pressurizing means and performing circulation step (circulating volume: 10 L/min) for about five minutes.

FIGS. 15 and 16 are graphs showing variations with times of the dissolved oxygen concentrations of the oxygen-containing water produced by the mixture fluid production device.

Dissolved oxygen concentration (unit is "ppm") is calibrated on the vertical axis of each of FIGS. 15 and 16, and elapsed time (unit is a "day") after oxygen is solubilized by mixing oxygen with water by the mixing device 10 in the mixture fluid production device and then discharged is calibrated on the horizontal axis.

In FIG. 15, plot "▲" is the average value of saturated-dissolved oxygen concentration in water having a temperature of 20° C.

A curve plotted by "●" shows variations with times of the dissolved oxygen concentrations in a case where water having dissolved oxygen concentration of 35.62 ppm by mixing oxygen with water by the mixing device of the mixture fluid production device according to the invention is stored in an open container (for example, a beaker).

A curve plotted by "■" shows variations with times of the dissolved oxygen concentrations in a case where water having dissolved oxygen concentration of 35.63 ppm by mixing oxygen with water by the mixing device of the mixture fluid production device according to the invention is stored in a container in which an opening portion is closed by a lid (for example, a bin closed by a lid).

In FIG. 16, plot "▲" is the average value of saturated-dissolved oxygen concentration in water having a temperature of 20° C.

A curve plotted by "●" shows variations with times of the dissolved oxygen concentrations in a case where water having dissolved oxygen concentration of 50.96 ppm by mixing oxygen with water by the mixing device 10 of the mixture fluid production device according to the invention is stored in an open container (for example, a beaker).

A curve plotted by "■" shows variations with times of the dissolved oxygen concentrations in a case where water having dissolved oxygen concentration of 50.96 ppm by mixing oxygen with water by the mixing device of the mixture fluid production device according to the invention is stored in a container in which an opening portion is closed by a lid (for example, a bin closed by a lid).

A curve plotted by "x" shows the dissolved oxygen concentration when oxygen water (dissolved oxygen concentration that is marked is 40 ppm) produced by a pressurizing method of the related art is opened for dissolved oxygen measurement. In the pressurizing method of the related art, a commercially available high-concentration oxygen dissolution device (DAIEI Co., Ltd.: product name "Enzyme Fighter OD-110 type") was used and oxygen was pressure-mixed with water by feeding pure oxygen into a tank of the device and setting the internal pressure of the tank to be in a range of 0.1 Mpa to 0.5 Mpa.

It is confirmed from FIGS. 15 and 16 that in the water (water mixed with oxygen) produced by the mixture fluid production device according to the invention, the amount of dissolved oxygen is large, and even if a long time (35 days or more) elapses after mixing, the amount of dissolved oxygen is the amount of dissolved oxygen far exceeding the amount of saturated-dissolved oxygen of the water. On the other hand, in a product (oxygen water) produced by the pressurizing method of the related art, even if dissolved oxygen concentration at the time of pressurization is 40 ppm, at the point of time of opening, dissolved oxygen concentration sharply decreases to a range of 8 ppm to 9 ppm, thereby becoming the same as the saturated-dissolved oxygen of normal water (FIG. 16). That is, according to the mixture fluid production device related to the invention, it is possible to produce water with dissolved oxygen stabilized, which cannot be realized in the prior art.

Here, if a person drinks water which is produced by the mixing device, is easily absorbed into the body, and contains a very large amount of dissolved oxygen, oxygen can be easily taken in the body. For this reason, by drinking the water with a very large amount of dissolved oxygen, it is possible to easily and stably supplement oxygen into the body of a person who needs oxygen supply for the reason of a decrease in lung function or the like.

In addition, if the water with a very large amount of dissolved oxygen is used, it is possible to easily perform nurture or culture of an animal, a plan, and a microorganism which need oxygen supply, other than a human being.

REFERENCE SIGNS LIST

1: outer peripheral edge portion
2: concave portion
3: central portion
4: through-hole
5: casing (casing on the supply side)
6: casing (casing on the discharge side)
7: supply pipe
8: discharge pipe
10: mixing device
20: lid section
100: mixture fluid production device
G: mixing section
M: main body
P, P1 to P8: pin

The invention claimed is:

1. A production method of a mixture fluid that includes a first liquid-phase fluid and one kind or two or more kinds among a solid, a gas, and a second liquid-phase fluid different from the first liquid-phase fluid, the production method comprising:
providing a mixture fluid production device comprising a pump and a mixing device comprising a disk-shaped mixing section that mixes the first liquid-phase fluid with the one kind or two or more kinds among the solid, the gas, and the second liquid-phase fluid, the disk-shaped mixing section including a supply hole for a fluid, a discharge hole for the fluid, a flow path that makes the supply hole and the discharge hole communicate with each other, and a plurality of columnar pins, the pins protruding from a disk portion of the disk-shaped mixing section and ultra-vibrating by contact with the fluid, wherein the supply hole is disposed in a vicinity of a center of the disk-shaped mixing section and the discharge hole is disposed in a vicinity of an outer peripheral edge of the disk-shaped mixing section, or the discharge hole is disposed in the vicinity of the center of the disk-shaped mixing section and the supply hole is disposed in the vicinity of the outer peripheral edge of the disk-shaped mixing section, wherein an annular row that is formed by the pins disposed on a concentric imaginary circle is disposed in each of plural rows toward the outer peripheral edge of the disk-shaped mixing section from the center of the disk-shaped mixing section, and the pins are disposed radially toward the outer peripheral edge of the disk-shaped mixing section from the center of the disk-shaped mixing section, wherein a diameter D of each of the pins has a relationship of 0.004 R≤D≤0.089 R, where R represents a radius of the disk-shaped mixing section, and wherein a fluid that includes materials to be mixed is supplied from the supply hole to the flow path, mixed due to cavitation of the fluid that is generated by ultra-vibration of the pins when passing through the flow path with the contact with the pins, and discharged from the discharge hole;
a supply step of supplying the fluid that includes materials to be mixed from the supply hole of the disk-shaped mixing section to the flow path by pressurizing the fluid that includes materials to be mixed, by the pump; and
a mixing and discharge step in which the fluid is mixed due to cavitation of the fluid that is generated by ultra-vibration of the pins of the disk-shaped mixing section due to the contact with the fluid when the fluid passes through the flow path with the contact with the pins, and discharged from the discharge hole.

2. The production method of a mixture fluid according to claim 1, wherein in the supply step, the fluid is supplied at a pressure of greater than or equal to 0.1 MPa.

3. The production method of a mixture fluid according to claim 1, wherein the materials to be mixed are a liquid-phase fluid and a gas, the liquid-phase fluid being water, and the gas being oxygen.

4. A nurture or culture method of an animal, a plant, or a microorganism comprising:
providing oxygen water produced by the production method according to claim 3 to the animal, the plant, or the microorganism.

5. A production method of a mixture fluid that includes a first liquid-phase fluid and one kind or two or more kinds among a solid, a gas, and a second liquid-phase fluid different from the first liquid-phase fluid, the production method comprising:
providing a mixture fluid production device comprising a pump, a material storage tank, a material transport line, and a mixing device comprising a disk-shaped mixing section that mixes the first liquid-phase fluid with the one kind or two or more kinds among the solid, the gas, and the second liquid-phase fluid, the disk-shaped mixing section including a supply hole for a fluid, a discharge hole for the fluid, a flow path that makes the supply hole and the discharge hole communicate with each other, and a plurality of columnar pins, the pins protruding from a disk portion of the disk-shaped mixing section and ultra-vibrating by contact with the fluid, wherein the supply hole is disposed in a vicinity of a center of the disk-shaped mixing section and the discharge hole is disposed in a vicinity of an outer peripheral edge of the disk-shaped mixing section, or the discharge hole is disposed in the vicinity of the center of the disk-shaped mixing section and the supply hole is disposed in the vicinity of the outer peripheral edge of the disk-shaped mixing section, wherein an annular row that is formed by the pins disposed on a concentric imaginary circle is disposed in each of plural rows toward the outer peripheral edge of the disk-shaped mixing section from the center of the disk-shaped mixing section, and the pins are disposed radially toward the outer peripheral edge of the disk-shaped mixing section from the center of the disk-shaped mixing section, wherein a diameter D of each of the pins has a relationship of 0.004 R≤D≤0.089 R, where R represents a radius of the disk-shaped mixing section, and wherein a fluid that includes materials to be mixed is supplied from the supply hole to the flow path, mixed due to cavitation of the fluid that is generated by ultra-vibration of the pins when passing through the flow path with the contact with the pins, and discharged from the discharge hole;
a supply step of supplying the fluid that includes materials to be mixed from the supply hole of the disk-shaped mixing section to the flow path by pressurizing the fluid that includes materials to be mixed, by the pump; and
a mixing and discharge step in which the fluid is mixed due to cavitation of the fluid that is generated by ultra-vibration of the pins of the disk-shaped mixing section due to the contact with the fluid when the fluid passes through the flow path with the contact with the pins, and discharged from the discharge hole, wherein the mixture fluid discharged from the mixing device can be circulated to the material storage tank through the material transport line, and the supply step and the mixing and discharge step are repeatedly performed by circulating the mixture fluid discharged from the discharge hole of the disk-shaped mixing section of the mixing device through the supply step and the mixing and discharge step to the material storage tank through the material transport line and supplying the mixture fluid from the supply hole of the disk-shaped mixing section of the mixing device again.

6. A production method of oxygen water, the production method comprising:
providing a mixture fluid production device comprising a pump and a mixing device comprising a disk-shaped mixing section that mixes a first liquid-phase fluid with one kind or two or more kinds among a solid, a gas, and a second liquid-phase fluid different from the first liquid-phase fluid, the disk-shaped mixing section including a supply hole for a fluid, a discharge hole for the fluid, a flow path that makes the supply hole and the discharge hole communicate with each other, and a plurality of columnar pins, the pins protruding from a disk portion of the disk-shaped mixing section and ultra-vibrating by contact with the fluid, wherein the supply hole is disposed in a vicinity of a center of the disk-shaped mixing section and the discharge hole is disposed in a vicinity of an outer peripheral edge of the disk-shaped mixing section, or the discharge hole is disposed in the vicinity of the center of the disk-shaped mixing section and the supply hole is disposed in the vicinity of the outer peripheral edge of the disk-shaped mixing section, wherein an annular row that is formed by the pins disposed on a concentric imaginary circle is disposed in each of plural rows toward the outer peripheral edge of the disk-shaped mixing section from the center of the disk-shaped mixing section, and the pins are disposed radially toward the outer peripheral edge of the disk-shaped mixing section from the center of the disk-shaped mixing section, wherein a diameter D of each of the pins has a relationship of $0.004 R \leq D \leq 0.089 R$, where R represents a radius of the disk-shaped mixing section, and wherein a fluid that includes materials to be mixed is supplied from the supply hole to the flow path, mixed due to cavitation of the fluid that is generated by ultra-vibration of the pins when passing through the flow path with the contact with the pins, and discharged from the discharge hole;
a supply step of supplying oxygen-containing water from the supply hole of the disk-shaped mixing section to the flow path by pressurizing the oxygen-containing water by the pump; and
a dissolution and discharge step in which, when the oxygen-containing water passes through the flow path with the contact with the pins of the disk-shaped mixing section, oxygen is dissolved in water due to cavitation that is generated by ultra-vibration of the pins due to the contact with the oxygen-containing water, and oxygen water in which a state where a dilute concentration of dissolved oxygen is greater than or equal to 25 ppm lasts 35 days or more in air is discharged from the discharge hole.

* * * * *